US011819713B2

(12) United States Patent
Tinaz et al.

(10) Patent No.: US 11,819,713 B2
(45) Date of Patent: *Nov. 21, 2023

(54) MULTI-FREQUENCY ULTRASOUND THERAPY SYSTEM WITH DATA ENCODER

(71) Applicant: Profound Medical Inc., Mississauga (CA)

(72) Inventors: Levant Tinaz, Etobicoke (CA); Patrick Leonard, Toronto (CA); Xiaoyu Zhang, Mississauga (CA); Ron Kurtz, Oakville (CA); Mathieu Allard, Mississauga (CA)

(73) Assignee: Profound Medical Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,552

(22) Filed: Nov. 15, 2022

(65) Prior Publication Data

US 2023/0072545 A1    Mar. 9, 2023

Related U.S. Application Data

(62) Division of application No. 16/516,492, filed on Jul. 19, 2019, now Pat. No. 11,547,876.

(Continued)

(51) Int. Cl.
*A61N 7/00* (2006.01)
*B06B 1/06* (2006.01)
(Continued)

(52) U.S. Cl.
CPC .............. *A61N 7/02* (2013.01); *B06B 1/0276* (2013.01); *B06B 1/0607* (2013.01);
(Continued)

(58) Field of Classification Search
CPC .............. A61N 7/02; A61N 2007/0073; A61N 2007/0078; B06B 1/0276; B06B 1/0607; B06B 2201/176
See application file for complete search history.

(56) References Cited

U.S. PATENT DOCUMENTS 9,925,000 B2    3/2018   Bek et al.
11,547,876 B2 *  1/2023   Tinaz ...................... A61N 7/02
(Continued)

FOREIGN PATENT DOCUMENTS

WO    2013165935 A1    11/2013

OTHER PUBLICATIONS

ISA, "International Search Report", PCT/IB2019/000854, dated Jan. 23, 2020.

(Continued)

*Primary Examiner* — Boniface Ngathi
(74) *Attorney, Agent, or Firm* — Intrinsic Law Corp.

(57) ABSTRACT

A multi-frequency ultrasound therapy apparatus is configured to operate at its center frequency and at the higher harmonic of its center frequency. The center frequency can be for the entire apparatus or for each ultrasound source element. At least one source element can generate ultrasound energy at its center frequency while, simultaneously, at least another source element can generate ultrasound energy at the higher harmonic of its center frequency. In addition, the same source element can generate ultrasound energy at its center frequency and the higher harmonic of its center frequency, respectively, but at different times. A data storage unit that stores encrypted and encoded data is disposed on the apparatus. The encoded data includes a unique identification code of the apparatus, the condition of use of the apparatus, the center frequency of each source element, the (Continued)

ultrasound efficiency of each source element, and/or other parameters relating to the apparatus.

13 Claims, 7 Drawing Sheets

Related U.S. Application Data

(60) Provisional application No. 62/820,038, filed on Mar. 18, 2019.

(51) Int. Cl.
*B06B 1/02* (2006.01)
*A61N 7/02* (2006.01)

(52) U.S. Cl.
CPC ............... *A61N 2007/0073* (2013.01); *A61N 2007/0078* (2013.01); *B06B 2201/76* (2013.01)

(56) References Cited

U.S. PATENT DOCUMENTS

| 2006/0058664 | A1 | 3/2006 | Barthe et al. |
| 2012/0209118 | A1 | 8/2012 | Warnking |
| 2012/0271294 | A1 | 10/2012 | Barthe et al. |
| 2013/0303904 | A1 | 11/2013 | Barthe et al. |
| 2014/0236049 | A1 | 8/2014 | Barthe et al. |
| 2014/0276055 | A1 | 9/2014 | Barthe et al. |
| 2014/0316269 | A1 | 10/2014 | Zhang et al. |
| 2015/0105701 | A1 | 4/2015 | Mayer et al. |
| 2015/0127038 | A1 | 5/2015 | Kawashima et al. |
| 2017/0209718 | A1 | 7/2017 | Tanis et al. |

OTHER PUBLICATIONS

Extended European Search Report for EP Application No. 19920076.7 dated Nov. 11, 2022.

* cited by examiner

MULTI-FREQUENCY ULTRASOUND THERAPY SYSTEM WITH DATA ENCODER

RELATED APPLICATIONS

This application is a divisional of U.S. patent application Ser. No. 16/516,492, titled "Multi-Frequency Ultrasound Therapy System With Data Encoder," filed on Jul. 19, 2019, which claims priority to U.S. Provisional Patent Application No. 62/820,038, titled "Multi-Frequency Ultrasound Therapy System With Data Encoder," filed on Mar. 18, 2019, which are hereby incorporated by reference.

TECHNICAL FIELD

The present application relates to thermal therapy systems, and particularly to the construction and operation of an ultrasound thermal therapy systems.

BACKGROUND

Ultrasonic transducers have been employed in ultrasound therapy systems to achieve therapeutic heating of diseased and other tissues. Arrays of ultrasound transducers operate to form a beam of ultrasonic energy that causes a conversion of sound to thermal energy in the effected tissue areas or treatment volumes, and a subsequent beneficial rise in the temperature in the treatment volumes. With proper monitoring of the heating effect, ultrasound therapy systems can be used to treat harmful cells and to controllably destroy cancerous tumors.

Ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezo-electric transducer crystal material which comes in several forms.

Various designs for ultrasonic therapy systems have been used in the present field of art. Ultrasound therapy system design can be challenging, and improvements to such designs would improve the effectiveness, safety, and/or cost to manufacture such systems.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an ultrasound therapy apparatus comprising an ultrasound therapy array having a plurality of ultrasound transducer elements; and a data storage unit configured to store encrypted and encoded data representing a unique identification code for said ultrasound therapy apparatus; and a parameter for said ultrasound transducer elements.

In one or more embodiments, the parameter includes a frequency value representing a predetermined center frequency for said ultrasound transducer elements. In one or more embodiments, said predetermined center frequency is defined for the ultrasound therapy array as a whole. In one or more embodiments, said predetermined center frequency is defined for each transducer element individually based at least on respective physical dimensions of each respective transducer element. In one or more embodiments, said ultrasound therapy array configured and arranged to receive electrical driving input signals from a power supply, and further configured and arranged to provide ultrasonic energy output at least at said predetermined center frequency and a higher harmonic of said predetermined center frequency.

In one or more embodiments, said encrypted and encoded data includes a date of use of said apparatus. In one or more embodiments, said encrypted and encoded data indicate a condition of use of said apparatus. In one or more embodiments, said condition of use functions as an interlock for said apparatus when said condition of use indicates that the apparatus has been used. In one or more embodiments, said unique identification code comprises a serial number of the apparatus. In one or more embodiments, said unique identification code comprises a model designation of said apparatus. In one or more embodiments, an encoded software or hardware revision number for said apparatus. In one or more embodiments, said encoded data includes a transducer efficiency of each transducer element. In one or more embodiments, said data storage unit is addressable and machine readable and said data storage unit further comprises a data interface configured and adapted for at least reading said encoded data from the data storage unit.

Another aspect of the invention is directed to a multi-frequency ultrasound therapy apparatus comprising an ultrasound therapy array having a plurality of ultrasound transducer elements; wherein each transducer element: (a) has an operational bandwidth spanning at least a center frequency through an integer multiple of said center frequency, (b) is defined by a respective set of physical dimensions, and (c) is defined by a respective transducer efficiency proportional to the respective transducer element's acoustic power output relative to said respective transducer element's electrical power input; and an electrical driving circuit configured and arranged for electrical coupling to said ultrasound therapy array; said electrical driving circuit configured and arranged to selectively deliver a first electrical driving signal to a first transducer element at said center frequency, and further configured to deliver a second electrical driving signal to a second transducer element at an integer multiple of said center frequency.

In one or more embodiments, said electrical driving circuit is configured and arranged to simultaneously deliver said first and second electrical driving signals to said first and second transducer elements, respectively, said first transducer element different than said second transducer element. In one or more embodiments, said electrical driving circuit is configured and arranged to deliver, at different times, said first and second electrical driving signals to said first and second transducer elements, respectively, said first transducer element being the same as said second transducer element.

In one or more embodiments, the apparatus further comprises a data storage unit configured to store encoded data representing a predetermined center frequency for each transducer element, wherein the electrical driving circuit is configured to obtain the predetermined center frequency from the data storage unit and to generate the electrical driving signals using the predetermined center frequency.

Another aspect of the invention is directed to a method for operating a multi-frequency ultrasound therapy apparatus, comprising: electrically coupling a power control unit to a data storage unit disposed on the ultrasound therapy apparatus, the data storage unit storing encoded data representing a condition of use of the ultrasound therapy apparatus; with a processor in the power control unit, determining said condition of use of the ultrasound therapy apparatus; and when the condition of use indicates that the ultrasound therapy apparatus has been used, interlocking the ultrasound therapy apparatus to prevent the processor from turning on any ultrasound transducer elements on the ultrasound therapy apparatus.

In one or more embodiments, the method further comprises when the condition of use indicates that the ultrasound therapy apparatus has not been used: delivering a first electrical driving signal to a first transducer element at a center frequency of the first transducer element; and delivering a second electrical driving signal to a second transducer element at a higher harmonic of a center frequency of the second transducer element. In one or more embodiments, the method further comprises simultaneously delivering the first and second electrical driving signals to the first and second transducer elements, wherein the first transducer element is different than the second transducer element. In one or more embodiments, the method further comprises delivering at different times the first and second electrical driving signals to the first and second transducer elements, wherein the first transducer element is the same as the second transducer element.

In one or more embodiments, the method further comprises with the processor in the power control unit, determining the center frequency of the first and second transducer elements, the encoded data in the data storage unit including a predetermined center frequency of each transducer element; with the power control unit, generating electrical driving signals for the first and second transducer elements based, at least in part, on the predetermined center frequency of the first and second transducer elements.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

Figure 1:
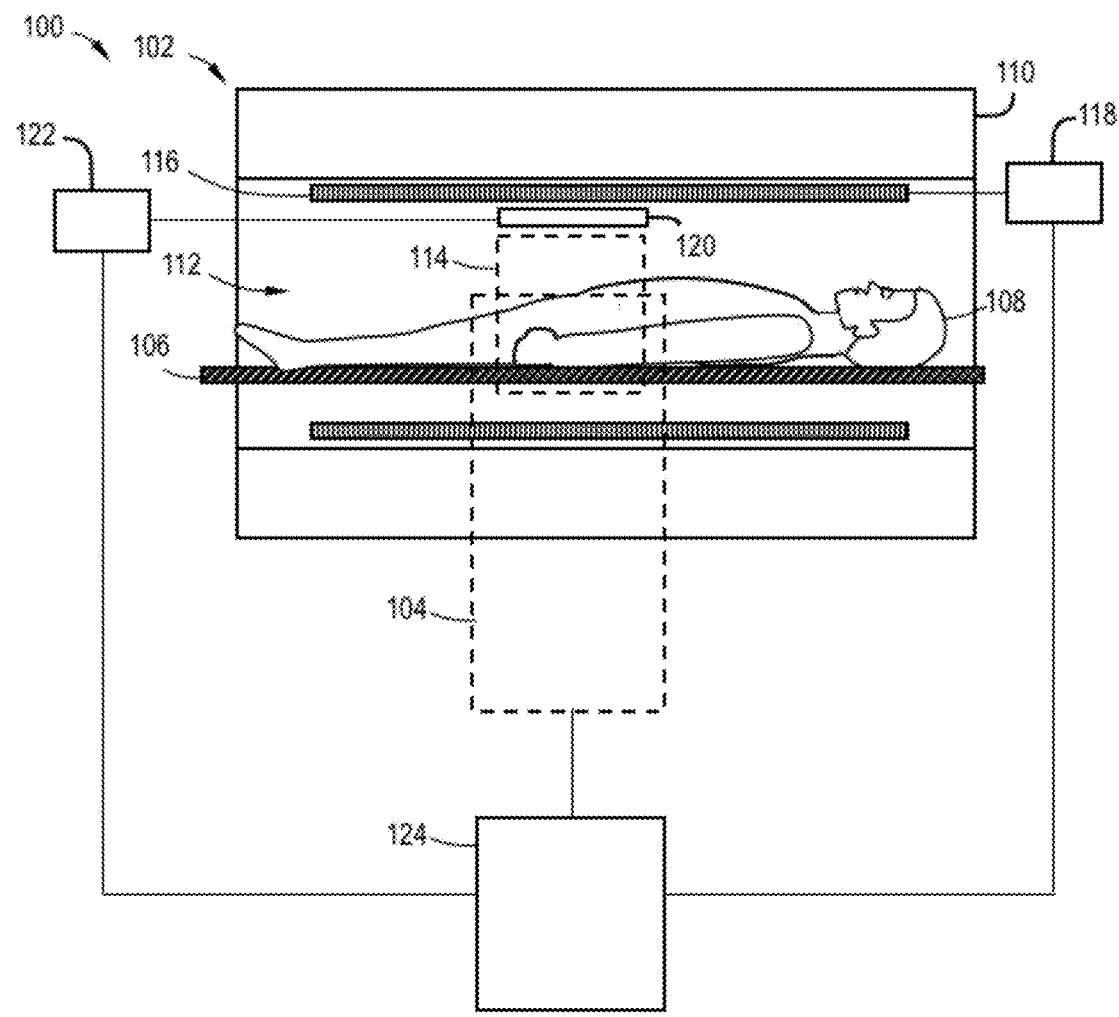
FIG. 1 is a diagram of a medical system in which at least some of the apparatus, systems, and/or methods disclosed herein are employed, in accordance with at least some embodiments.

A multi-frequency ultrasound thermal therapy apparatus is provided. The apparatus in various embodiments is configured to operate for example at the center frequency (f0), at the higher harmonic of the center frequency (3f0), and/or at other non-harmonic frequencies. The center frequency can be for the apparatus as a whole (i.e., for the entire ultrasound transducer array on the apparatus) or for each individual ultrasound source element. The center frequency for each ultrasound source element is determined by the material of the ultrasound source element and its physical dimensions (e.g., the size of the dimension of the transducer source element that changes in response to an electrical driving signal).

In general, the center frequency is the most energy-efficient frequency at which to operate. A combination of the center frequency and its higher harmonic can be used to ablate a target volume based on the desired depth of treatment. Since absorption of ultrasound in tissue is proportional (to the square) of the ultrasound frequency, the depth of treatment within the target volume can be controlled by operating at the center frequency or the higher harmonic of the center frequency. For example, higher-frequency ultrasound (e.g., 3f0) is absorbed by or deposited in the tissue closer to the ultrasound source element while lower-frequency ultrasound (e.g., f0) is absorbed by or deposited in tissue that is deeper or further away from the ultrasound source element.

It is to be understood that some transducers may operate somewhat outside a center frequency or may not be resonant. In this case, we can assign some first frequency of operation to be called for the present purposes the center frequency. That is, even in a system where there is not physically defined center frequency f0, we can define an operating frequency and call this the "center frequency" f0 for the present purposes. Integer multiples of this frequency (e.g., 2f0, 3f0, etc.) can then be defined as well, which the present disclosure will adopt as a way of reference. In some embodiments, the range of operation of the transducer may span at least this f0 frequency through at least some multiple thereof (whether or not a resonance center frequency on account of the physics of the transducer).

In some embodiments, the ultrasound transducer array can operate with one or more ultrasound source elements generating ultrasound at its/their center frequency while one or more ultrasound source elements simultaneously generate ultrasound at the higher harmonic of its/their center frequency. In other embodiments, the ultrasound transducer array can operate with one or more ultrasound source elements generating ultrasound at its/their center frequency and, at a later time, one or more of the same ultrasound source elements can generate ultrasound at the higher harmonic of its/their center frequency. In some embodiments, the ultrasound transducer array can operate with one or more ultrasound source elements generating ultrasound at its/their center frequency while one or more ultrasound source elements simultaneously generate ultrasound at a harmonic of its/their center frequency. In addition or in the alternative to any of the foregoing, one or more ultrasound source elements can generate ultrasound one or more other non-harmonic frequencies which may be used for imaging, detecting tissue properties, electrical integrity testing, or other purposes.

A data storage unit can be disposed on the ultrasound thermal therapy apparatus. The data storage unit is configured to store encoded data that represents a unique identifier of the apparatus, a condition of use of the apparatus, a date of use of the apparatus, the center frequency of the apparatus, the center frequency of each ultrasound source element in the ultrasound transducer array, and/or the ultrasound efficiency of the ultrasound source elements at f0 and 3f0. The data storage unit can encode additional data as described herein. In some embodiments, the RF driving circuit generates driving signals, for an ultrasound source element, that have a frequency equal to the predetermined center frequency stored in the data storage unit, and/or equal to the higher harmonic of the predetermined center frequency stored in the data storage unit.

The condition of use indicates whether the apparatus has been used previously. If the apparatus has been used previously, the condition of use can function as an interlock that prevents the RF driving circuit from delivering driving signals to the ultrasound source elements. A "used" condition of use can also function as a signal that causes a computer operatively coupled to the data storage unit to display a warning message and/or generate a warning light and/or sound. It is desirable to prevent the RF driving circuit from delivering driving signals to the ultrasound source elements because the ultrasound thermal therapy apparatus is generally a single-use device.

FIG. 1 is a diagram of a medical system 100 in which at least some of the apparatus, systems, and/or methods disclosed herein are employed, in accordance with at least some embodiments. The system 100 includes a patient support 106 (on which a patient 108 is shown), a magnetic resonance system 102 and an image-guided energy delivery system 104.

The magnetic resonance system 102 includes a magnet 110 disposed about an opening 112, an imaging zone 114 in which the magnetic field is strong and uniform enough to perform magnetic resonance imaging, a set of magnetic field gradient coils 116 to change the magnetic field rapidly to enable the spatial coding of MRI signals, a magnetic field gradient coil power supply 118 that supplies current to the magnetic field gradient coils 116 and is controlled as a function of time, a transmit/receive coil 120 (also known as a "body" coil) to manipulate the orientations of magnetic spins within the imaging zone 114, a radio frequency transceiver 122 connected to the transmit/receive coil 120, and a computer 124, which performs tasks (by executing instructions and/or otherwise) to facilitate operation of the MRI system 102 and is coupled to the radio frequency transceiver 122, the magnetic field gradient coil power supply 118, and the image-guided energy delivery system 104. The image-guided energy delivery system 104 includes a therapeutic applicator, such as an ultrasound applicator, to perform image-guided therapy (e.g., thermal therapy) to treat a treatment volume as described herein.

The MRI computer 124 can include more than one computer in some embodiments, which can be dedicated to the MRI system 102. In at least some embodiments, the MRI computer 124 and/or one or more other computing devices (not shown) in and/or coupled to the system 100 may also perform one or more tasks (by executing instructions and/or otherwise) to implement one or more aspects and/or embodiments disclosed herein (or portion(s) thereof) such as to control the driving or operating frequency of the ultrasound elements in the therapeutic applicator at the center frequency (f0) and the higher harmonic (3f0) of the center frequency (3f0).

One or more of the computers, including computer 124, can include a treatment plan for and/or program instructions for determining a treatment plan (e.g., in real time) for the patient 108 that includes the target treatment volume and the desired or minimal energy (e.g., thermal) dose for the target treatment volume. The treatment plan can also include the desired operating or driving frequency of the ultrasound elements, such as f0 and/or 3f0. The computer(s) can use images from the magnetic resonance system 102 to image guide the rotational position and insertion-retraction position of the therapeutic applicator. In some embodiments, one or more dedicated computers control the image-guided energy delivery system 104. Some or all of the foregoing computers can be in communication with one another (e.g., over a local area network, a wide area network, a cellular network, a WiFi network, or other network), for example through a software-controlled link to a communication network.

In some embodiments, the treatment plan includes a set of initial parameters for driving each ultrasound element such as its initial frequency, initial phase, and initial amplitude. These parameters can be updated in real time based on the measured temperature of the target volume, for example as determined by MR thermometry.

Figure 2:
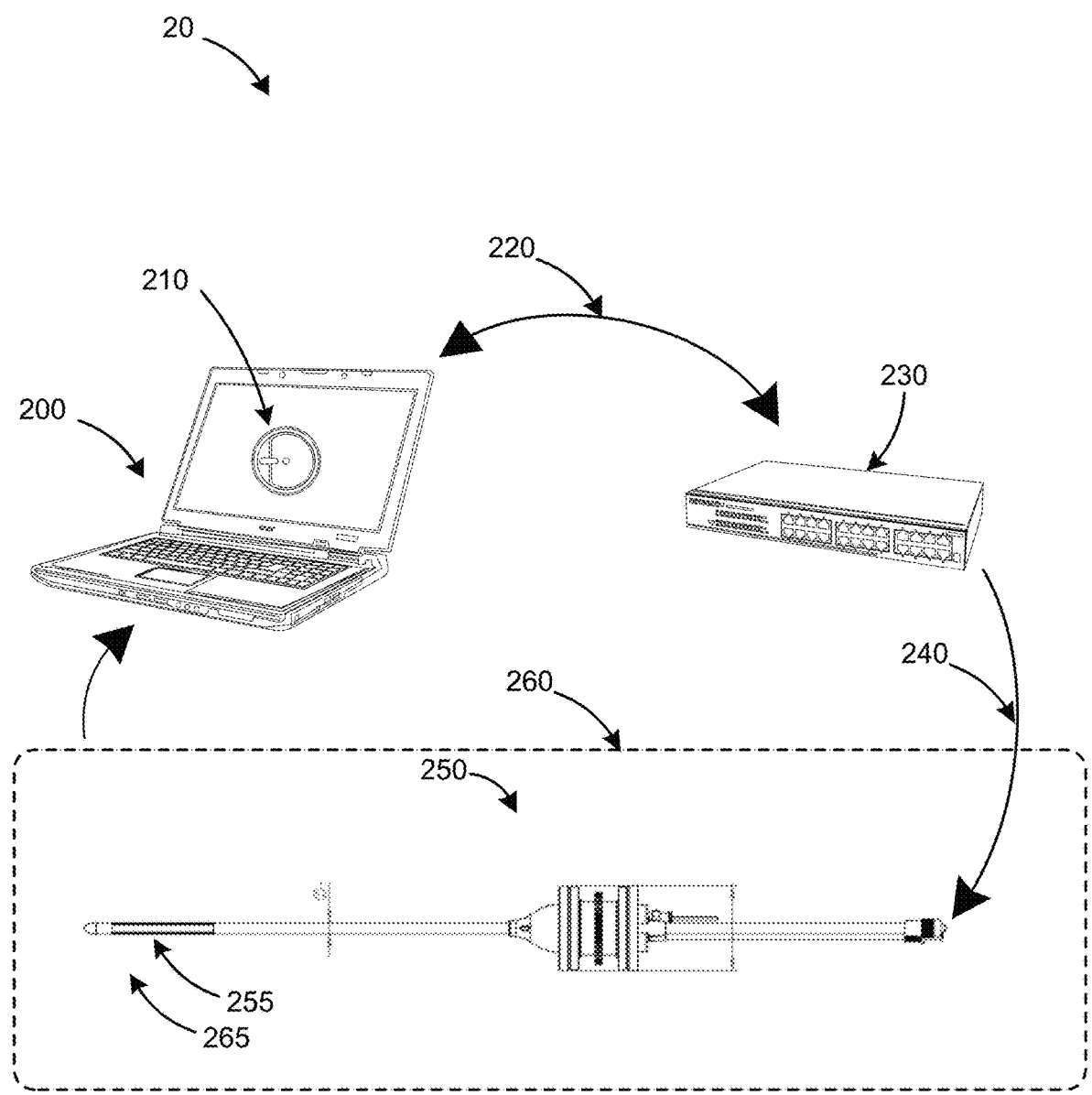
FIG. 2 is a simplified illustration of an exemplary image-guided energy delivery system according to one or more embodiments.

FIG. 2 is a simplified illustration of an exemplary image-guided energy delivery system 20 according to one or more embodiments. The image-guided energy delivery system 20 can be the same as or different than image-guided energy delivery system 104. The system 20 includes a master computer 200, such as a portable PC, workstation, or other processing device having a processor, memory, and coupled to some input/output apparatus. Master computer 200 may include a display and may support a user interface 210 to facilitate control of and observation of the thermal therapy treatment process.

Master computer 200 is adapted for coupling to other systems and components through a computer interface connection 220. Connection 220 carries data and information to and from master computer 200 and may comprise standard or special-purpose electrical wiring connection cables, such as serial connection cables or the like. Also, connection 220 may be achieved wirelessly (e.g., via Bluetooth, WiFi, cellular, or other wireless connection), and may further be achieved by way of multiple connections, over a network, or by another suitable method.

Master computer 200 is coupled through connection 220 to a power control unit 230. Power control unit 230 may be implemented as a stand-alone hardware apparatus but may be implemented as a part of master computer 200, e.g., by being built onto a special card in a computer or server system that accommodates such hardware components. In addition, at least some of the functionality of the power control unit 230 can be achieved in software that can run on master computer 200 or another computer.

Power control unit 230 may specifically include at least a processor adapted for processing machine or program instructions, which may be provided to the processor from another component of system 20 and may be stored on a memory device in power control unit 230. Circuitry including analog and/or digital circuitry may be operated within power control unit 230 so as to determine an output power to one or more ultrasound therapy transducer elements in an ultrasound therapy apparatus 250.

In some embodiments, power control unit 230 may deliver controlled electrical driving signals to a plurality of ultrasound transducer elements (e.g., PZT array elements) in ultrasound therapy apparatus 250. The driving signals may be controlled to deliver a programmed amount of power to each element or to groups of elements of therapy apparatus 250. The driving signals may also be controlled so as to provide a determined driving voltage, current, amplitude, waveform, phase, and/or frequency (e.g., f0 and/or 3f0) to the ultrasonic transducers of therapy apparatus 250. Such electrical driving signals are carried from power control unit 230 to the ultrasound therapy apparatus 250 over suitable wires, cables, or buses 240. Appropriate plug interfaces or connectors may be included so as to mate the various ends of the connectors or buses to and from their associated components.

In operation, ultrasound therapy apparatus 250 includes a ultrasound array 255 at a distal portion 265 that is inserted into a portion of a patient's body to deliver a suitable dose of ultrasound energy to tissue in a diseased region of the patient's body.

The patient and the ultrasound therapy apparatus 250 are generally disposed in an imaging volume 260 such as within a magnetic resonance imaging (MRI) apparatus, which can provide (e.g., via MRI computer 124) real-time images of the relevant parts of the patient (e.g., the treatment volume) to master computer 200 or display and user interface 210. In some embodiments, real-time monitoring of the thermal therapy is performed so that a clinical operator can monitor the progress of the therapy within the treatment volume or diseased tissue. Manual or automated changes can be made to the power signals from power control unit 230 based on input from the results and progress of the treatment.

The feedback and coupling of the treatment system components to the control components in system 20 can be used to ensure that an optimum radio frequency (RF) power signal, including the optimal operating or driving frequency (e.g., f0 and/or 3f0) and/or phase is provided to each element of the ultrasound array 255 used in treatment of diseased tissues. Some examples include treatment of prostate cancer tumors in male patients using MRI guided ultrasound therapy applications.

RF power control unit 230 may include separate circuit cards having individual processors, amplifiers, filters and other components to achieve the desired driving power output to the elements of ultrasound array 255 of ultrasound treatment apparatus 250. Alternatively, a single processor may be employed to control the behavior of the various power channels to each array element.

Figure 3:
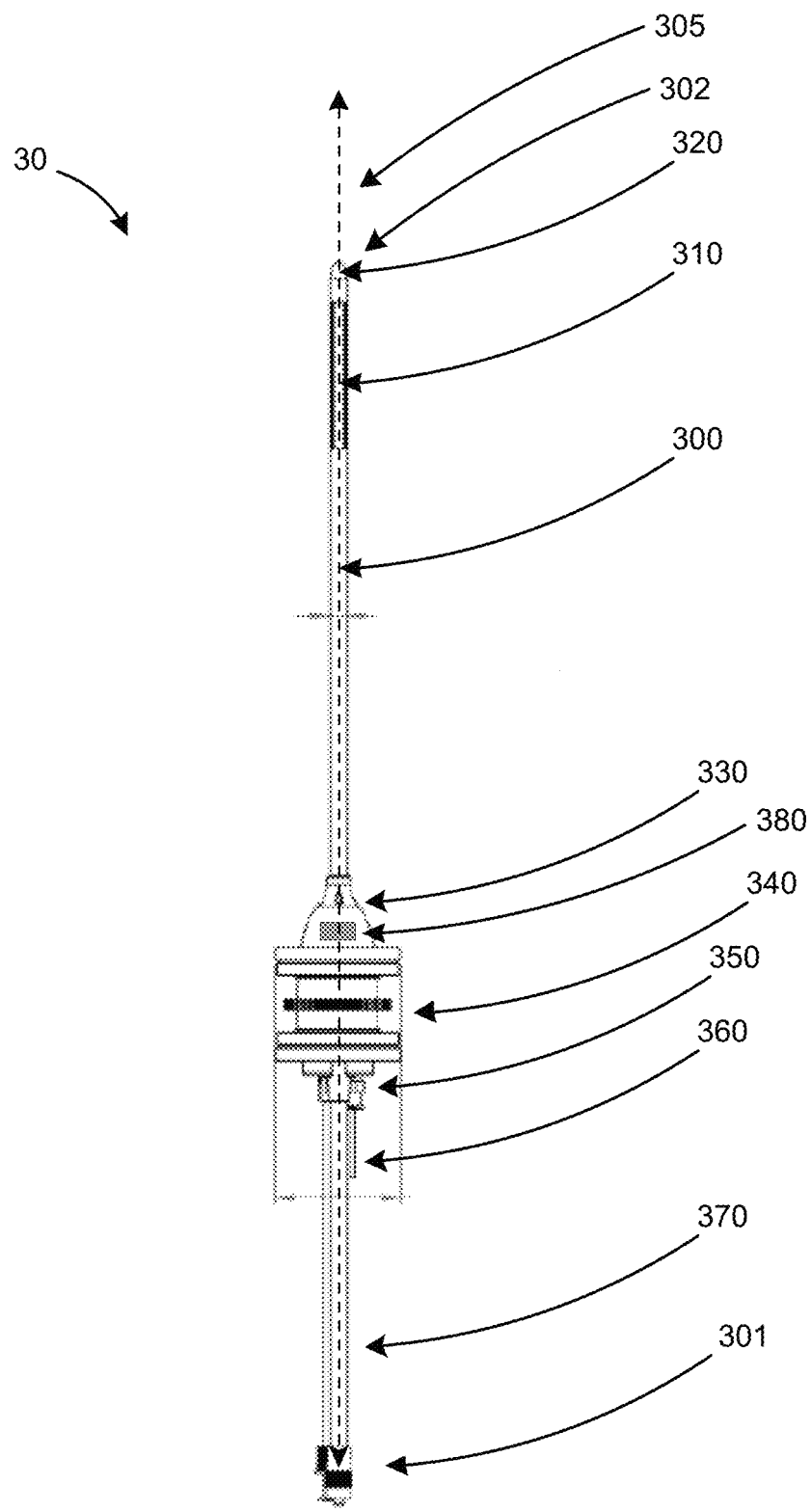
FIG. 3 illustrates an exemplary ultrasound therapy applicator according to one or more embodiments.

FIG. 3 illustrates an exemplary ultrasound therapy applicator 30 according to one or more embodiments. Applicator 30 can be the same as or different than ultrasound therapy apparatus 250 and/or can be included in image-guided energy delivery system 104. Applicator 30 includes an elongated shaft portion 300, which can be inserted into a body cavity proximal to a diseased tissue region of a patient. In some instances, elongated shaft portion 300 (or a portion thereof) may be inserted into the urethra of a male patient to treat diseased tissue such as cancerous tissue of the male prostate. The insertion of applicator 30 into the patient is done by pressing the applicator 30 into an appropriate patient channel or orifice, optionally using image guidance such as MRI or X-ray guidance to monitor the position of applicator 30 within the patient.

The applicator 30 has a proximal end 301 and a distal end 302. The proximal and distal ends 301, 302 define an axis 305 along which the applicator 30 is elongated. An ultrasound transducer array 310 (e.g., source elements) is disposed near, towards, and/or at the distal end 302 of the applicator 30. The source elements of the ultrasound transducer array 310 are oriented to face outwardly such that they radiate ultrasonic energy outwardly from the applicator 30 and axis 305 towards a target volume (e.g., a diseased tissue volume).

The applicator 30, or typically the elongated shaft portion 300, is inserted into the patient until the transducer array 310 reaches an area proximal to the diseased tissue volume or target volume for the thermal therapy. In this way, when power is provided to the transducer array 310 it will cause a controlled heating of the diseased tissue volume to treat the disease condition or affect some other desired outcome. Tip 320 may be constructed of blunt smooth material such as a polymer or metal material to assist in easy reduced friction insertion and movement of applicator 30 into the patient. In some embodiments, this design minimizes frictional stress on the interior walls of the patient's urethra. The tip 320 can also serve as a fiducial marker for locating the applicator 30 in MR (or other) images, such as through the construction of the tip 320 and/or the inclusion of an MRI-visible (e.g., an MR-opaque) material in the tip 320. In some embodiment, the tip 320 can be shaped (e.g. similar to a coudé catheter) so that it can be inserted easily in a natural orifice of the body such as the urethra.

In some embodiments, the applicator 30 includes features and/or materials to make it possible to see, in an MR image or other medical image, the location of the ultrasound window on the applicator 30 to facilitate proper alignment with the diseased tissue and to avoid treatment of critical anatomical structures.

A transition portion 330 of applicator 30 is flared or bulbous in shape and provides a safety zone that prevents unwanted portions of apparatus 30 from entering into the patient's body. Flanged portions of transition portion 330 allow for easier manipulation of applicator 30 and mechanical control of the same. The transition portion 330 can act as a handle for holding the applicator 30 and may be constructed of an optically-transparent material such as clear plastic. This can allow viewing of the interior of the applicator 30 in some situations to determine if any gas (e.g., air) bubbles have been trapped in the fluid circuit portion of the apparatus. The gas can then be vacated to minimize or avoid interference in the transmission of ultrasound energy from the transducer system or interference with the cooling fluid flow within the body of the system. The flanges can also provide a mechanical means for holding applicator 30 in place within a bearing system or rotation and translation driver used to move and rotate applicator 30 during operation.

A geared element 340 provides a mechanically-compatible actuation means for rotating applicator 30 within the patient's body so that array 310 is properly and controllably rotated about the long axis 305 of shaft 300 to treat a volume of tissue up to a complete 360-degree rotational volume surrounding the axis 305 of shaft 300 if desired. In some embodiments, a motor is adapted for driving the gear 340 of applicator 30 to provide such rotation of the applicator 30 within the patient about the long axis 305 of the applicator 30.

Mechanical interfaces 350 allow coupling of fluid intake and outtake connections to applicator 30 so that temperature-control fluid can be passed into and out of the applicator 30. For example, in situations where cooling of the applicator 30 itself or surrounding tissue in needed, the fluid can be applied to these interfaces optionally using standard fluid hook-up connectors and tubing 370. Also, electrical wiring 360 or micro-buses can be passed through interfaces 350 to provide electrical driving power to the elements of transducer array 310 and to receive sensor signals or other signals and data from the components of applicator 30. Again, standard electrical connectors may be used to interface outside power and control systems with the internal electrical elements of applicator 30. For example, the applicator 30 can include a temperature sensor for sensing a fluid in the applicator 30, such as the temperature-control fluid that circulates in the applicator 30 and/or an ultrasound-coupling fluid. The fluid can be in thermal equilibrium with the surrounding tissue in the patient's body. In addition or in the alternative, a temperature sensor can be disposed externally on the applicator 30 to sense the tissue temperature directly. The fluid temperature and/or the directly-measured temperature can be used as feedback and/or for error determination of the tissue temperature determined by MR thermometry.

An optional addressable and machine-readable data storage unit 380 can be disposed on or in the applicator 30. The data storage unit 380 can store, for example encoded in a data store, one or more parameters, values, and/or data related to the applicator 30. For example, the data storage unit 380 can store a unique identifier or a unique identification code for the applicator 30, the serial number of the applicator 30, its model number, its revision number (e.g., software revision number and/or hardware revision number), its date of manufacture, its date of use (if any), and/or its condition of use or use state (i.e., whether the applicator 30 has been used in any procedure). The data store can also store data or parameters relating to the transducer array 310 as described herein. In some embodiments, the data storage unit 380 can store the data in encrypted form to increase security (e.g., to prevent unauthorized reprogramming and/or reuse of the applicator 30). The data storage unit 380 can also be tamper-resistant or tamper-proof to prevent unauthorized reprogramming and/or reuse of the applicator 30.

The data storage unit 380 includes a data interface that allows the data storage unit 380 to send and receive signals. For example, the data interface can receive requests for data stored on the data storage unit 380 and requests to update or store new data on the data storage unit 380. Output data signals can be sent through the data interface to an external device, such as a computer that requested the data. The data interface can include a wired and/or a wireless communication interface. Examples of a wired interface include a serial port, a USB port, an Ethernet port, etc. Examples of a wireless interface include a radio for Bluetooth, WiFi, cellular, or other wireless connection, and may further be achieved by way of multiple connections, over a network, or by another suitable method.

In operation, applicator 30 may be placed with tip 320 proximal to an aperture in the patient's body and with the long axis 305 of shaft 300 substantially aligned with a cavity or channel (e.g., the urethra) of the patient for insertion therein. The applicator 30 is then automatically or manually or by a combination of the two inserted into the patient's body, beginning with tip 320 end of shaft 300. When the applicator 30 is sufficiently inserted into the patient's body (e.g., using image guided translation motor stages) the translation of applicator 30 is secured. Then, a computer-controlled thermal therapy procedure is undertaken, with applicator 30 being rotated about its long axis 305 within the patient's body so that transducer array 310 provides a therapeutic energy field such as an ultrasonic field of known strength, frequency, and duration to treat the diseased tissue proximal to array 310. When the thermal therapy is completed, power to ultrasound array 310 is removed and applicator 30 is retracted from the patient substantially along the long axis 305 of the applicator 30, in substantially the reverse direction as it was inserted.

Figure 4:
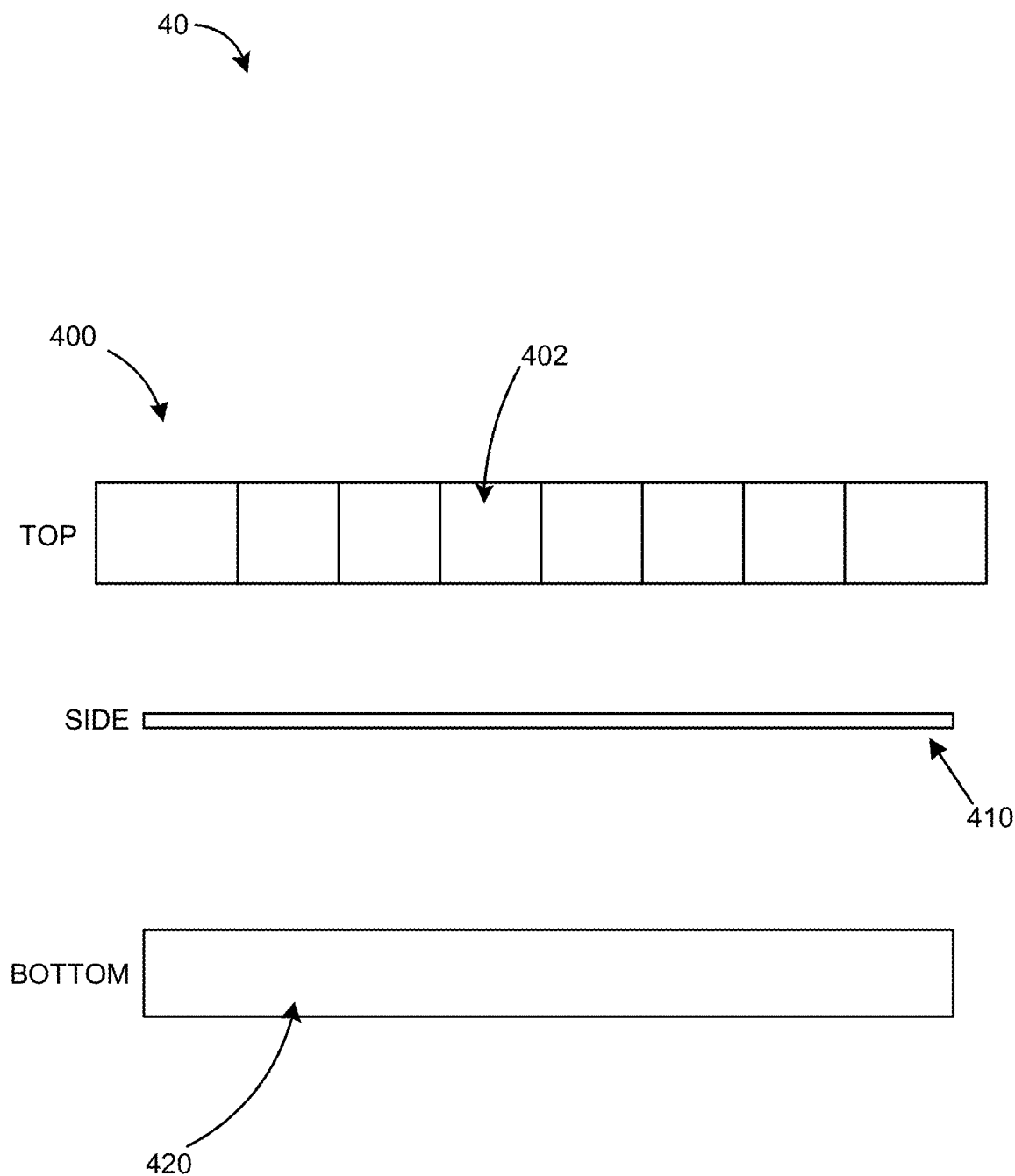
FIG. 4 illustrates an exemplary design for a transducer array according to one or more embodiments.

FIG. 4 illustrates an exemplary design for a transducer array (such as array 310 of FIG. 3) according to one or more embodiments. An ultrasonic array 40 is shown as it appears from the "top" face thereof at view 400. Note that in the present illustration the "top" face is the face of the array normally facing into the center of the applicator shaft and away from the patient's body. The same array is shown from the side in view 410. The opposing or "bottom" view of the array is shown in view 420, which is the face of the array which is outwardly directed at the patient's treatment volume and away from the applicator. It is seen that in this exemplary embodiment the ultrasonic array 40 is constructed from a substantially flat or relatively planar material. This may be a PZT-based material as is generally known to those skilled in the art. In some embodiments the material may comprise K320 from Piezo Technologies of Indianapolis, IN USA. Alternately, it may be made of PZ52 or a similar material from Ferroperm Piezoceramics of Kvistgaard, Denmark. The array and its elements may be designed and arranged to have a pre-determined optimal resonance or center frequency (f0), for example at about 4 MHz, or other central frequency for best penetration and power delivery to the diseased volume of tissue, in some embodiments, along with a harmonic thereof, such as the higher harmonic (3f0) at about 13 MHz as well.

According to the present embodiment, the front face of transducer array 40 is cut into a plurality of individual array elements, e.g., 402. The individual elements 402 may or may not all be of the same shape and size. In certain embodiments, the elements 402 are substantially rectangular or square in shape and provide an ultrasonic energy field proximal to the face of elements 402 as dictated by the design, material, and driving signals for the elements 402. The elements 402 of array 40 may be driven individually, in groups, and/or together in a programmed way to create an overall ultrasonic therapeutic energy field within a controlled volume of tissue in a patient. For example, the frequency, amplitude, phase, or relative phase of each element 402 may be driven individually, in groups, and/or together. The array 40 mounted to the rest of the therapy applicator may be rotated about the long axis of array 40 so as to provide treatment to a volume around array 40 as needed.

Both the front face 400 and the back face 420 of array 40 are silvered to permit delivery of driving power signals to and grounding of the elements of array 40. The ends and edges (shown in 410) of array 40 may be left unsilvered. In this way some or all of elements 402 may be powered by an appropriate power source.

In some embodiments, one or both elements at the ends of array 40 may be "dummy" elements that are not substantially driven or used for the actual thermal therapy in operation of the device.

Figure 5:
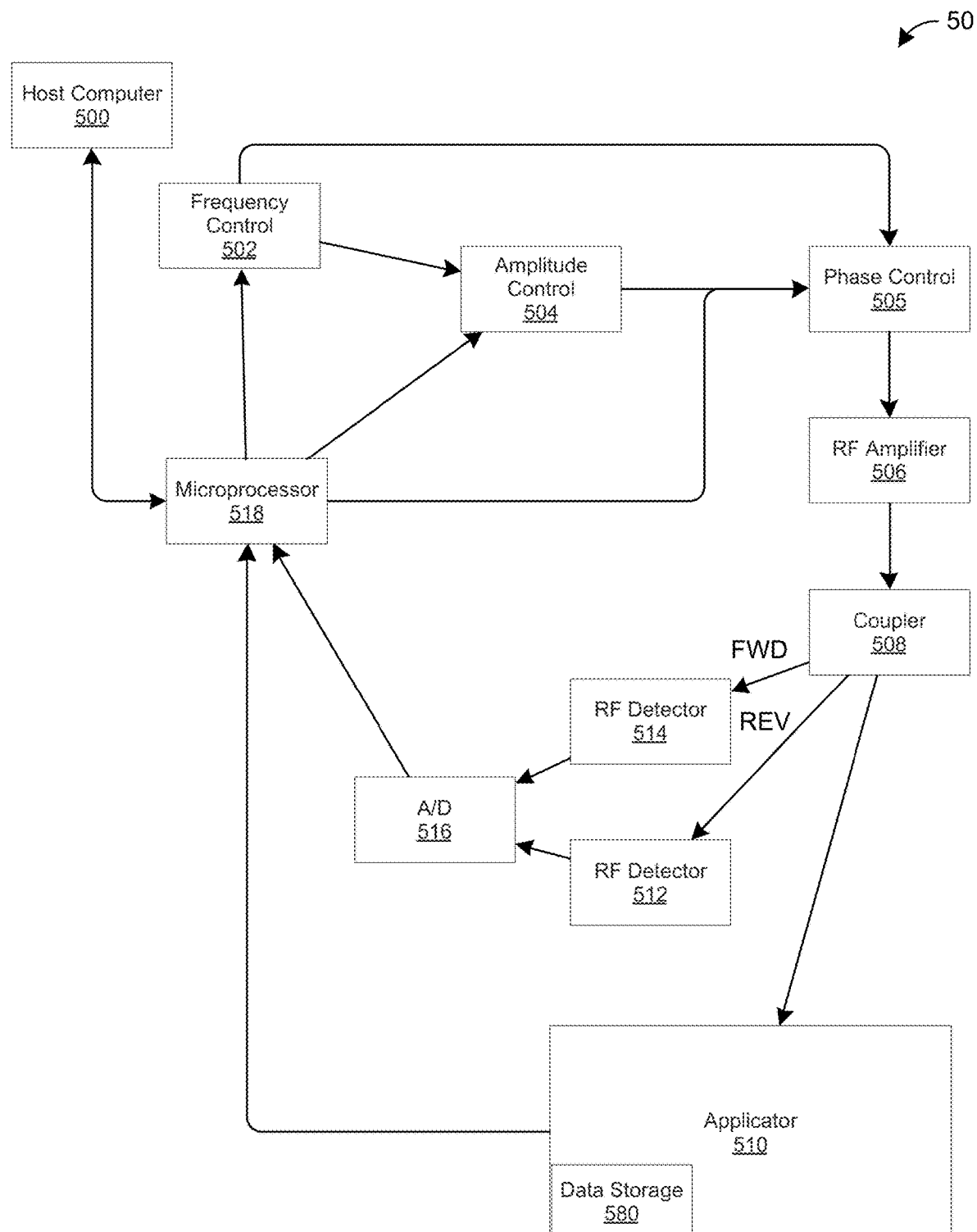
FIG. 5 illustrates an exemplary block diagram of a system for controlling the RF driving power to elements of an ultrasound treatment apparatus according to one or more embodiments.

FIG. 5 illustrates an exemplary block diagram of a system 50 for controlling the RF driving power to elements of an ultrasound treatment apparatus according to one or more embodiments. A host computer 500, which may be similar to master computer 200 of FIG. 2, requests a certain output power. The requested output power may be an output power required by the entire ultrasound treatment applicator 510, a single transducer element, or a group of elements. The power needed to accomplish an effective and safe ultrasound therapy treatment may involve the determination of actual power to be emitted from the array or elements of the array, and can optionally include comparing the actual power (or expected output power) with a threshold safe power level. The output power requested by the host computer 500 can include a requested frequency, amplitude, and/or phase.

The host computer 500 delivers the instruction or request for a certain driving power signal to microprocessor 518, which may be implemented in an integrated circuit (IC) within an RF power control unit, an application-specific IC (ASIC), or similar circuit that operates upon instructions, optionally from a group of instructions stored in some digital memory device in or coupled to microprocessor 518.

Microprocessor 518 provides an input signal to frequency control 502, amplitude control 504, and phase control 505 units. In some embodiments, the amplitude control unit 504 receives the microprocessor 518 output signal as well as an output signal from the frequency control unit 502. In some embodiments, the phase control unit 505 receives the microprocessor 518 output signal as well as an output signal from the frequency control unit 502 or the amplitude control unit 504.

According to one or more embodiments, amplitude control unit 504 provides an output to a radio frequency (RF) amplifier 506, which amplifies the amplitude of the driving signal to a level that is useful for driving the physical transducer elements of the ultrasound applicator 510.

A coupler 508 is provided to couple the output driving signals from the RF amplifier 506 to the treatment applicator 510 (or ultrasound array thereof). The reverse and forward powers from coupler 508 are provided to RF detectors 512 and 514, respectively, indicative of the actual power available from the transducer elements on the treatment applicator 510.

The RF detectors 512 and 514 provide an output to analog-to-digital (A/D) converter 516, which in turn informs microprocessor 518 of the reverse and forward output conditions at coupler 508. Accordingly, the power provided to treatment applicator 510 can be optimized and tuned to the precise levels needed to achieve a safe, effective, and reproducible ultrasound thermal therapy procedure. While MRI-based thermometry of a patient (e.g. of his prostate during treatment) may require a relatively long time (many seconds, several seconds), the present concepts allow rapid control of the power and frequency characteristics of the apparatus in the context of thermal therapy (e.g., of the prostate).

In some embodiments, microprocessor 518 may be in communication with host computer 500 to allow a more precise treatment routine in real-time, and/or to permit logging and recording of the specific electrical and physical conditions prevailing during the ultrasound therapy procedure.

In one or more embodiments, microprocessor 518 is programmed with the expected output power to the ultrasound treatment applicator. The system 50 is designed to output the expected power using the frequency control 502 and the amplitude control 504 blocks using the feedback from the RF detectors 512 and 514. In some embodiments, the microprocessor 518 takes the existing output power, the expected output power and the RF detector values for the forward and reverse readings and outputs the appropriate amplitude using a proportional control loop with delay. The algorithm may be implemented through a combination of hardware and software (instructions executed by the hardware).

A control loop using a proportional integral derivative (PID) controller or other controller may be employed for the present purpose in some embodiments. To reduce the noise inherent in these readings, the averaging of all inputs, or a select plurality of inputs, may be done with a circular buffer of individual readings. In some embodiments, the only aspect of the system 50 that is tightly calibrated are the RF detectors 512, 514, but this is not required in all embodiments.

In some embodiments, the microprocessor 518 can send input signals that cause one or more transducer elements on applicator 510 to operate at (e.g., to be driven at) its/their center frequency f0 and that cause one or more transducer elements on applicator 510 to operate at the higher harmonic of the center frequency (i.e., 3×f0 or 3f0). The center frequency f0 of a transducer element is the most energy-efficient frequency for the transducer element to operate. The center frequency f0 can be a function of the transducer element material (e.g., a piezoelectric material such as PZT) and the size of the dimension of the transducer element that changes in response to an electrical driving signal, for example the thickness of the transducer element or array indicated in view 410 of FIG. 4. The center frequency f0 can be the same or different for a given pair of ultrasound transducer elements in the ultrasound transducer array on applicator 510. In addition, the transducer element array can have its own center frequency, which can be the same as or different than the center frequency of a given ultrasound transducer element.

Since absorption of ultrasound in tissue is proportional (to the square) of the ultrasound frequency, the depth of treatment within the target volume can be controlled by operating a transducer element at f0 or 3f0. For example, higher-frequency ultrasound (e.g., 3f0) is absorbed or deposited closer to the source ultrasound transducer element while lower-frequency ultrasound (e.g., f0) is absorbed or deposited deeper or further away from the source ultrasound transducer element.

In one example, the microprocessor 518 can send input signals that simultaneously cause at least a first transducer element to operate at f0 and at least a second transducer element to operate at 3f0. In another example, the microprocessor 518 can send input signals that simultaneously cause one or more first groups of transducer elements to operate at f0 and one or more second groups of transducer elements to operate at 3f0. Each group of transducer elements can include transducer elements that are located adjacent to one another and/or transducer elements that are spaced apart from one another.

In yet another example, the microprocessor 518 can send input signals that cause at least a first transducer element to operate at f0 and at 3f0 but at different times (e.g., initially at f0 and then at 3f0, or initially at 3f0 and then at f0). In another example, the microprocessor 518 can send input signals that cause one or more groups of transducer element to operate at f0 and at 3f0 but at different times.

In another example, when a first group of transducer elements operates at f0, a second group of transducer elements can operate at f0 or at 3f0. The first and second groups of transducer elements can be driven (i.e., turned on) at the same time or there can be a delay between when the first group of transducer elements is turned on and when the second group of transducer elements is turned on. There can be an overlap in time when both the first and second groups of transducer elements are turned on at their respective frequencies. Likewise, the first and second groups of transducer elements can cease to be driven (i.e., turned off) at the same time or one group of transducer elements can be turned off at a first time while the other group of transducer elements can be turned off at a second time. After the first group of transducer elements operate at f0, at least one transducer element in the first group of transducer elements can operate at 3f0. Likewise, after the second group of transducer elements operate at f0 or 3f0, at least one transducer element in the second group of transducer elements can operate at 3f0 or f0 (i.e., at a different frequency than when the second group of transducer elements operate at f0 or 3f0). As described above, each group of transducer elements can include transducer elements that are located adjacent to one another and/or transducer elements that are spaced apart from one another.

In addition or in the alternative to any of the foregoing, the microprocessor 518 can send input signals that cause one or more transducer elements on applicator 510 to operate at one or more other non-harmonic frequencies (e.g., other than f0 and 3f0) which may be used for imaging, detecting tissue properties, electrical integrity testing, or other purposes.

Prior to or during operation, the microprocessor 518 can access encoded data stored on data storage unit 580 that is disposed on or in applicator 510. The data storage unit 580 can be the same as or different than data storage unit 380, discussed above, and some or all of the encoded data stored on data storage unit 380 can also be stored on data storage unit 580 (and vice versa). For example, prior to operation, the microprocessor 518 can request, from data storage unit 580, the date of use and/or the condition of use of applicator 510. If there is a date of use (e.g., other than the present day) or the condition of use is "used," the microprocessor 518 can cause a warning message to be displayed on the display of host computer 500 or another computer in network communication with microprocessor 518. In some embodiments, the warning message can prompt the user to enter the serial number of the applicator 510 to confirm that the data storage unit 580 is disposed in the correct applicator 510. In addition or in the alternative, if there is a date of use or the condition of use is "used," the microprocessor 518 can include program instructions (e.g., a flag or an interlock) that prevent it from turning on the transducer elements on applicator 510 (e.g., that prevent the microprocessor 518 from sending input signals for operating any of the transducer elements on applicator 510). In some embodiments, the data storage unit 580 can store the data in encrypted form to increase security (e.g., to prevent unauthorized reprogramming and/or reuse of the applicator 510). The data storage unit 580 can also be tamper-resistant or tamper-proof to prevent unauthorized reprogramming and/or reuse of the applicator 510.

The microprocessor 518 can also access, on the data storage unit 580, one or more parameters relating to the transducer elements on applicator 510. For example, the microprocessor 518 can send a request to data storage unit 580 to obtain the predetermined center frequency (f0) of one, some, or all transducer elements on applicator 510, which the microprocessor 518 can use when generating input signals to frequency control unit 502 (e.g., as part of generating electrical driving signals for the respective transducer elements). In another example, the microprocessor 518 can send a request to data storage unit 580 to obtain the transducer efficiency at f0 and/or at 3f0 for one, some, or all transducer elements on applicator 510. The transducer efficiency can be determined by the following equation:

$$\eta = \frac{P_{acoustic}}{P_{electric}} \quad (1)$$

where $P_{acoustic}$ is the acoustic power output by the transducer element and $P_{electric}$ is the electric power input to the transducer element. The transducer efficiency and the predetermined center frequency of each transducer element can be used in treatment planning.

Figure 6:
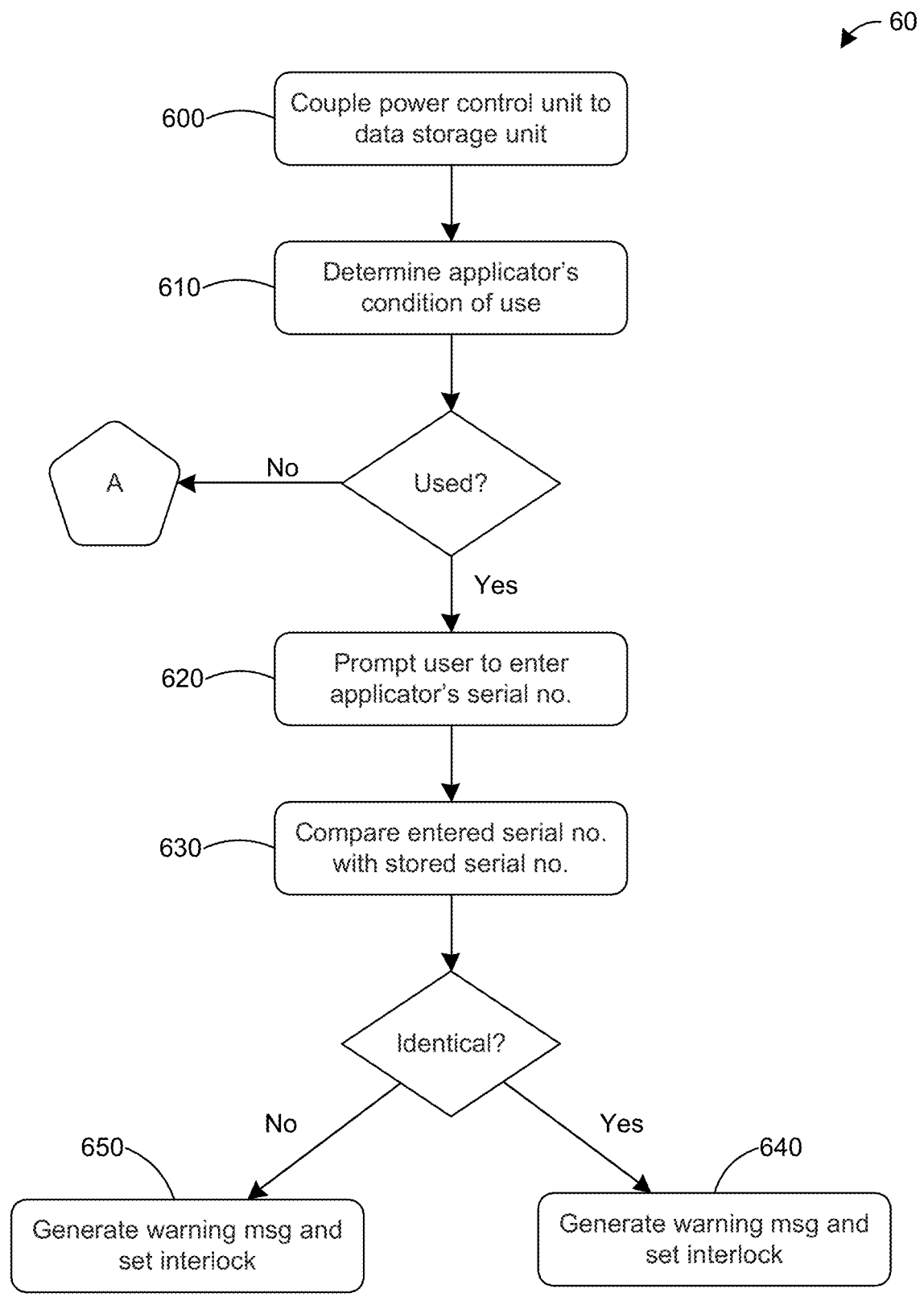
FIGS. 6 and 7 illustrate a flow chart of a method for operating a therapeutic applicator according to one or more embodiments.
Figure 7:
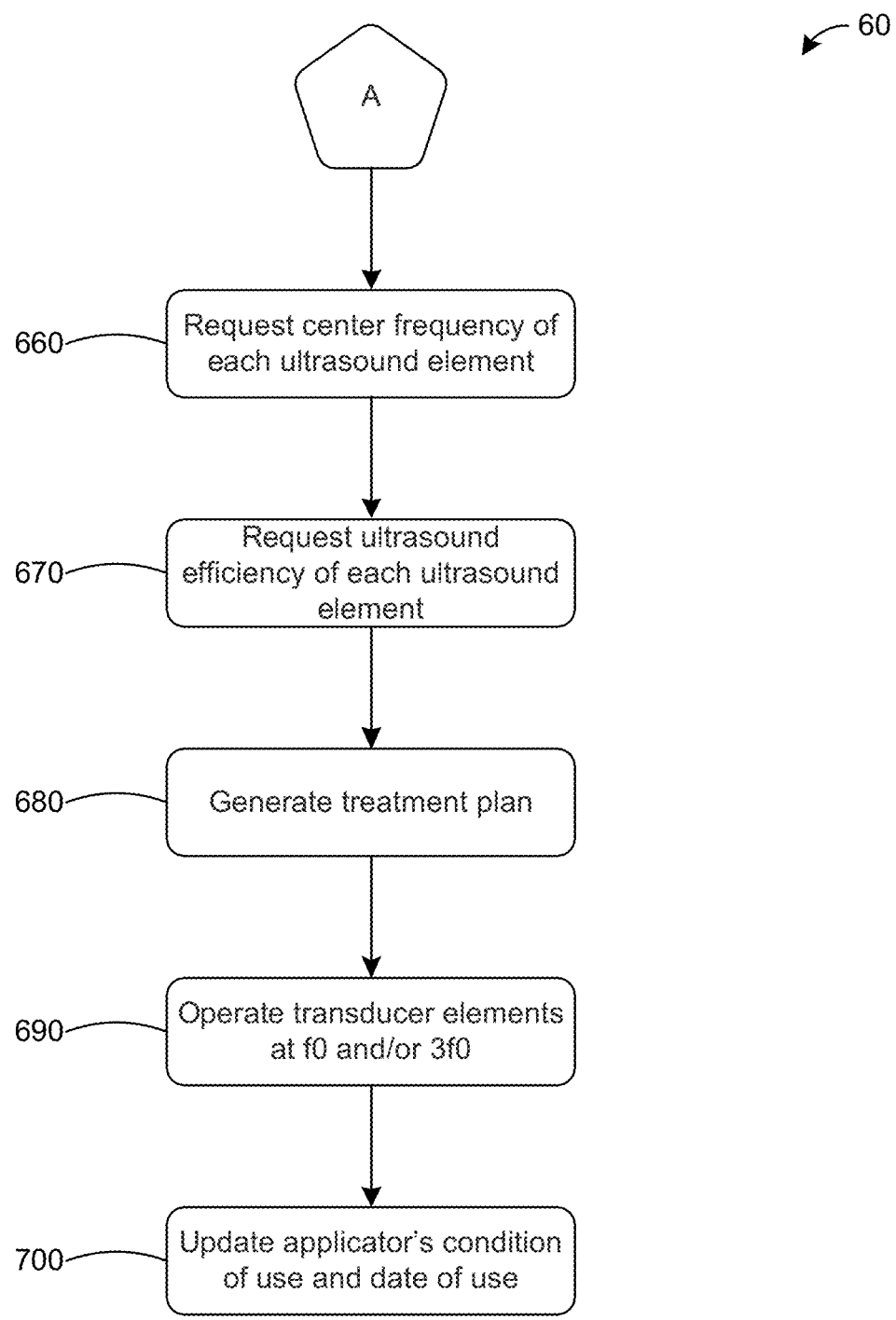

FIGS. 6 and 7 illustrate a flow chart 60 of a method for operating a therapeutic applicator according to one or more embodiments. In step 600, a power control unit, such as system 50, is electrically coupled to a data storage unit in the therapeutic applicator. The data storage unit can be the same as or different than data storage unit 380 and/or 580. For example, the data storage can store data in encrypted form to increase security (e.g., to prevent unauthorized reprogramming and/or reuse of the applicator). The data storage unit can also be tamper-resistant or tamper-proof to prevent unauthorized reprogramming and/or reuse of the applicator.

In step 610, a processor in the power control unit, such as microprocessor 518, determines the applicator's condition of use for example by sending a request to or querying the data storage unit. If the applicator's condition of use is "used" and/or the date of use is other than the present date, the flow chart 60 proceeds to step 620 to prompt the user to enter the applicator's serial number. After the user enters the applicator's serial number, the processor compares the entered applicator serial number with the stored serial number in step 630. If the serial numbers are identical, in step 640 the processor generates a warning message to inform the user that the present applicator has already been used (and thus should not be used if the applicator is single use). If the serial numbers are not identical, in step 650 the processor generates a warning message to inform the user that the data storage unit is not disposed on the correct applicator. In either case, the processor generates a soft interlock (i.e., a software-based interlock) in steps 640 and 650 that prevents the transducer elements on the applicator from being turned on. In some embodiments, steps 620 and 630 are optional, in which case the flow chart 60 proceeds directly to step 640 after the processor in the power control unit determines that the applicator's condition of use is "used" and/or the date of use is other than the present date.

In some embodiments, the therapy applicator device is designed for single (one-time) use only. So in an aspect, the data are written to a tamper-resistant data storage location in the applicator to avoid unwanted or unintentional re-writing of said data. For example, an encrypted set of information may be encoded and written to the storage location to avoid reprogramming the same in an attempt to reuse a therapy applicator that should not be reused, or to alter the date-used information.

Returning to step 610, if the condition of use is "unused" the flow chart 60 proceeds to placeholder A, which continues on FIG. 7. In step 660, the processor requests the center frequency of each transducer element from the data storage element on the applicator, the center frequency being stored in the data storage element as an encoded predetermined center frequency. In step 670, the processor requests the ultrasound efficiency of each transducer element from the data storage element on the applicator. In step 680, the processor (or other computer in network communication therewith) generates or updates a treatment plan based on the data obtained in steps 660 and 670. In step 690, thermal therapy is provided to the target volume in the patient while operating the transducer elements at f0 and/or 3f0, according to the stored values of the predetermined center frequency in the data storage element and according to the treatment plan, as described herein. For example, the treatment plan can be updated in real time during treatment based on feedback information, such as the measured temperature of the target volume (e.g., based on MR thermometry). In step 700, the processor updates the data storage element such that the applicator's condition of use is "used" and the applicator's date of use is the present date.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. A multi-frequency ultrasound therapy apparatus comprising:
   an ultrasound therapy array having a plurality of ultrasound transducer elements, wherein each transducer element: (a) has an operational bandwidth spanning at least a center frequency through an integer multiple of said center frequency, (b) is defined by a respective set of physical dimensions, and (c) is defined by a respective transducer efficiency proportional to the respective transducer element's acoustic power output relative to said respective transducer element's electrical power input;
   an electrical driving circuit configured and arranged for electrical coupling to said ultrasound therapy array, said electrical driving circuit configured and arranged to selectively deliver a first electrical driving signal to a first transducer element at said center frequency, and further configured to deliver a second electrical driving signal to a second transducer element at an integer multiple of said center frequency; and
   a data storage unit configured to store encoded data representing:
      a predetermined array center frequency for the ultrasound therapy array as a whole, and
      an element predetermined center frequency for each said ultrasound transducer element,
   wherein the electrical driving circuit is configured to obtain the element predetermined center frequency for each said ultrasound transducer element from the data storage unit and to generate the electrical driving signals using the element predetermined center frequency.

2. The apparatus of claim 1, wherein said electrical driving circuit is configured and arranged to simultaneously deliver said first and second electrical driving signals to said first and second transducer elements, respectively, said first transducer element different than said second transducer element.

3. The apparatus of claim 1, wherein said electrical driving circuit is configured and arranged to deliver, at different times, said first and second electrical driving signals to said first and second transducer elements, respectively, said first transducer element being the same as said second transducer element.

4. The apparatus of claim 1, wherein the electrical driving circuit is configured to obtain the predetermined array center frequency from the data storage unit and to generate the electrical driving signals using the predetermined array center frequency.

5. A method for operating a multi-frequency ultrasound therapy apparatus, comprising:
   electrically coupling a power control unit to a data storage unit disposed on the ultrasound therapy apparatus, the ultrasound therapy apparatus including an ultrasound therapy array having a plurality of ultrasound transducer elements, the data storage unit storing:
      encrypted and encoded data representing a condition of use of the ultrasound therapy apparatus,
      a predetermined array center frequency for the ultrasound therapy array as a whole, and
      an element predetermined center frequency for each said ultrasound transducer element;
   with a processor in the power control unit, determining said condition of use of the ultrasound therapy apparatus;
   when the condition of use indicates that the ultrasound therapy apparatus has been used, interlocking the ultrasound therapy apparatus to prevent the processor from turning on any ultrasound transducer elements on the ultrasound therapy apparatus;
   when the condition of use indicates that the ultrasound therapy apparatus has not been used, requesting, with the processor from the data storage unit, the element predetermined center frequency for each said ultrasound transducer element.

6. The method of claim 5, further comprising:
   when the condition of use indicates that the ultrasound therapy apparatus has not been used:
      delivering a first electrical driving signal to a first transducer element at a center frequency of the first transducer element; and
      delivering a second electrical driving signal to a second transducer element at a higher harmonic of a center frequency of the second transducer element.

7. The method of claim 6, further comprising simultaneously delivering the first and second electrical driving signals to the first and second transducer elements, wherein the first transducer element is different than the second transducer element.

8. The method of claim 6, further comprising delivering at different times the first and second electrical driving signals to the first and second transducer elements, wherein the first transducer element is the same as the second transducer element.

9. The method of claim 6, further comprising with the power control unit, generating electrical driving signals for the first and second transducer elements based, at least in part, on the element predetermined center frequency of the first and second transducer elements.

10. The method of claim 6, further comprising updating, with the processor, a treatment plan based on the element predetermined center frequency for each said ultrasound transducer element.

11. The method of claim 6, wherein:
   the data storage unit stores an ultrasound efficiency for each said ultrasound transducer element, and
   the method further comprises requesting, with the processor from the data storage unit, the ultrasound efficiency for each said ultrasound transducer element.

12. The method of claim 11, further comprising updating, with the processor, a treatment plan based on the element predetermined center frequency for each said ultrasound transducer element and the ultrasound efficiency for each said ultrasound transducer element.

13. The method of claim 12, further comprising updating, with the processor, the condition of use to indicate that the ultrasound therapy apparatus has been used.

* * * * *